United States Patent [19]

Wong et al.

[11] Patent Number: 5,000,731
[45] Date of Patent: Mar. 19, 1991

[54] SHUNTING DEVICE ADOPTED IN THE INTRACRANIAL SHUNTING SURGICAL OPERATION FOR THE TREATMENT OF HYDROCEPHALUS

[75] Inventors: Tai-Ting Wong, 7th Fl., No. 320-3, Shin Pai Rd., Sec. 2; Liang-Shong Lee; Gregory C. Niu, all of Taipei, Taiwan

[73] Assignee: Tai-Ting Wong, Taiwan

[21] Appl. No.: 336,865

[22] Filed: Mar. 30, 1989

[51] Int. Cl.$^5$ ............................................... A61M 5/00
[52] U.S. Cl. ................................................ 604/8; 604/9
[58] Field of Search .................... 604/8, 9, 129, 366, 604/53, 93

[56] References Cited

U.S. PATENT DOCUMENTS

| | | | |
|---|---|---|---|
| 3,583,387 | 6/1971 | Garner | 604/8 |
| 3,861,396 | 1/1975 | Vaillancourt | 604/129 |
| 4,787,885 | 11/1988 | Binder | 604/8 |

Primary Examiner—Robert A. Hafer
Assistant Examiner—Kerry Owens
Attorney, Agent, or Firm—Cushman, Darby & Cushman

[57] ABSTRACT

This invention relates to a shunting device adopted in the intracranial shunting surgical operation for the treatment of hydrocephalus. It is comprised of a thin film and a ventricular tube to be implanted into the cranium of a patient with hydrocephalus, which will bypass the intraventricular cerebrospinal fluid (CSF) in the brain of such a patient, and thus maintain a normal pressure inside the cranium for the treatment of hydrocephalus.

2 Claims, 4 Drawing Sheets

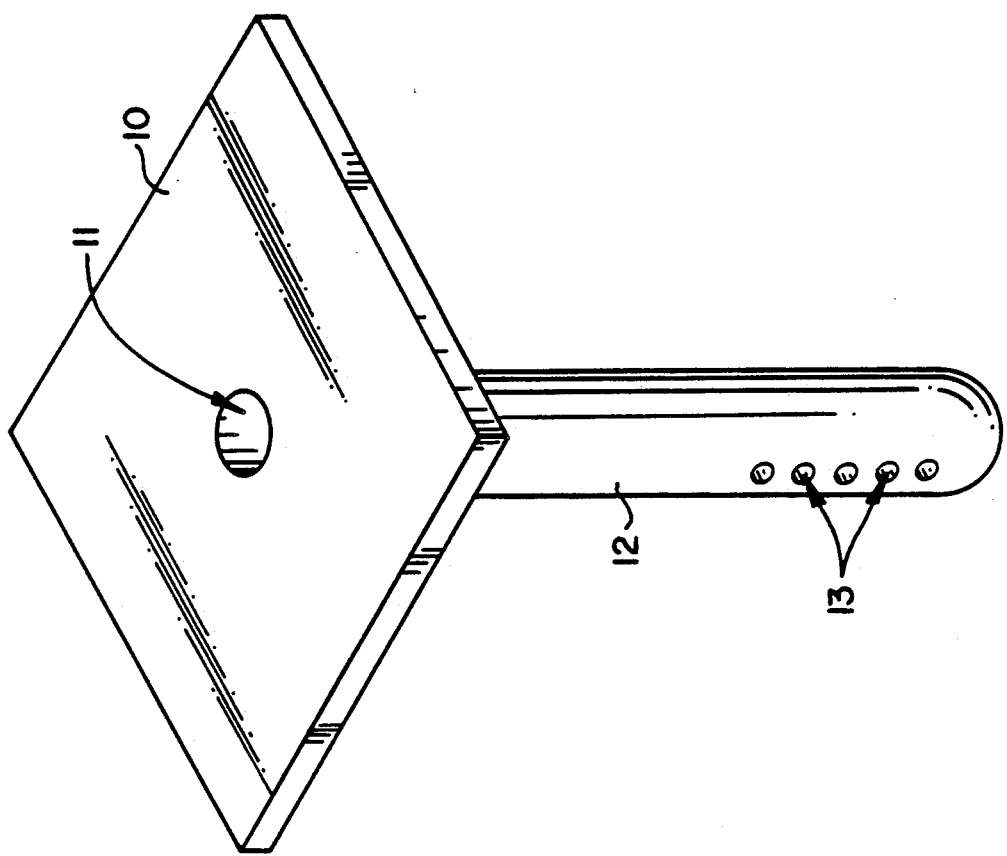
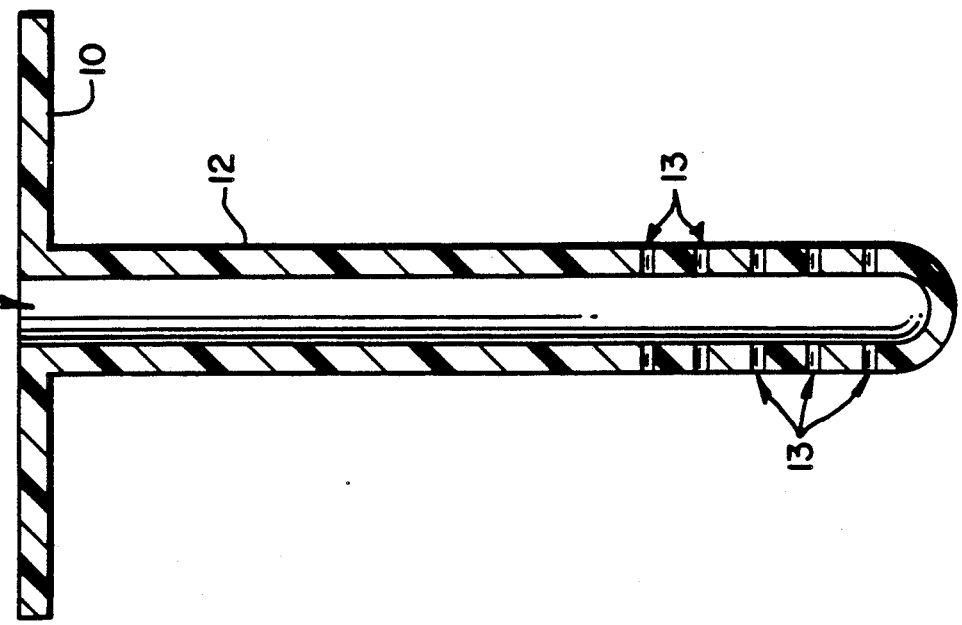

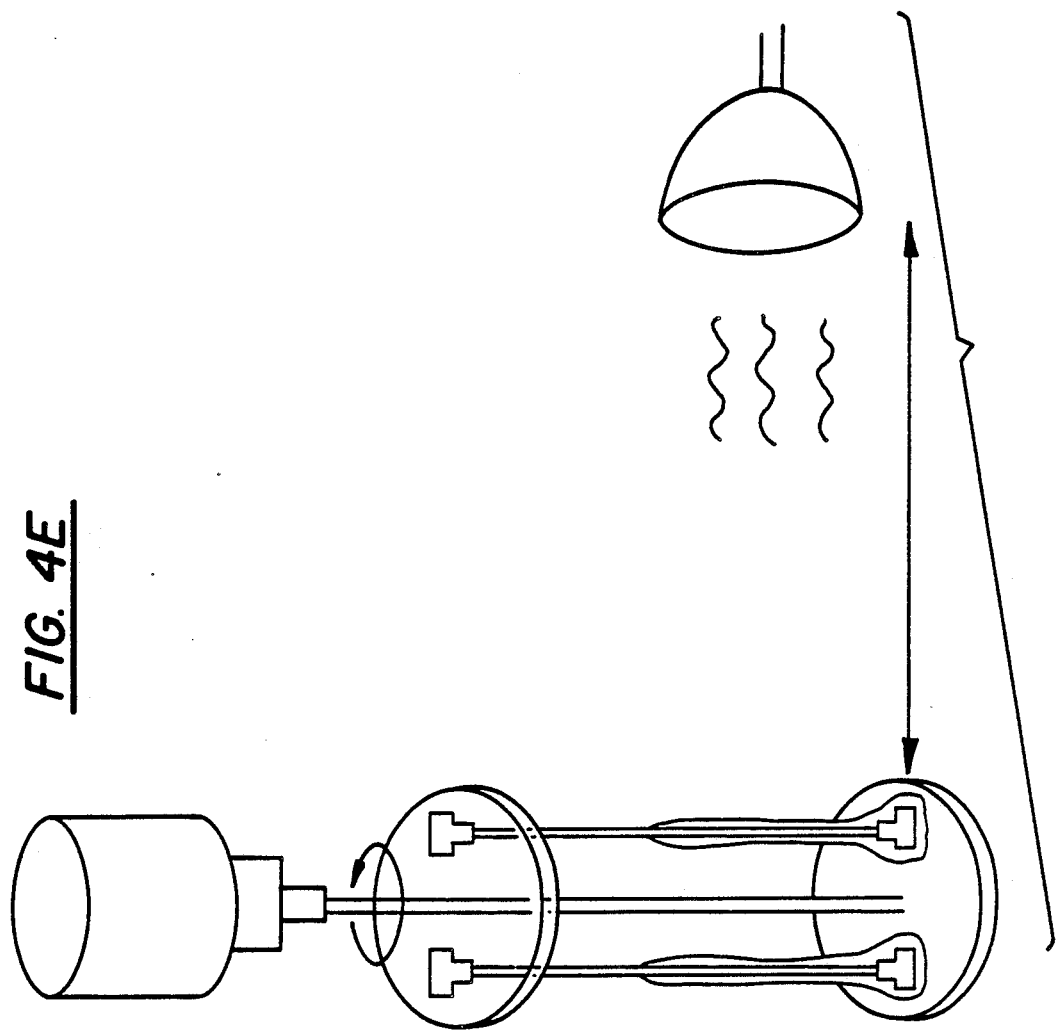
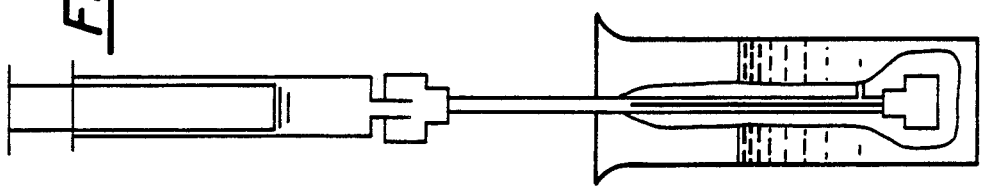

SHUNTING DEVICE ADOPTED IN THE INTRACRANIAL SHUNTING SURGICAL OPERATION FOR THE TREATMENT OF HYDROCEPHALUS

BACKGROUND AND SUMMARY

The ventricular system of the brain of human beings may be divided into the lateral ventricles, Monro's foramen, the third ventricle, aquaeduct, the fourth ventricle, foramen of Luschka, foramen of Magendie, etc. The subarachnoid spaces are located at the exterior of the brain and the spinal cord. The enlarged subarachnoid spaces located at the base of the brain are referred to as cisterns. The cerebrospinal fluid (hereinafter, CSF) is produced in the ventricular system and the subarachnoid spaces, and circulates within the ventricular system, the cisterns, the subarachnoid spaces, and finally to the arachnoid villi of the dural venous sinuses (sagittal sinus). The CSF is then absorbed through the venous sinuses into the blood circulation. If it is obstructed, the CSF will gradually increase and cause expansion of the ventricular system, the elevation of intracranial pressure, and the clinical symptoms of acute or chronic elevation of increased intracranial pressure. This condition referred to as hydrocephalus in medical science.

From the above description, it can be seen that hydrocephalus originates from obstruction to the circulation of CSF. It is generally treated by cutting off the obstruction focus, or bypassing the obstructed part by means of a shunting device, which is referred to as a hydrocephalus shunting procedure. Shunting procedures may be divided into extracranial shunting procedures and intracranial shunting procedures.

The theory of extracranial shunting procedures is to shunt the CSF to extracranial tissues or organs, where it can be absorbed by them. Of course, such a procedure is not consistent with normal CSF circulation and absorption physiology.

In extracranial shunting procedures, an extracranial shunting tube comprised of the intracranial and extracranial parts is used. The surgical operation may include : ventriculo-atrial shunt, ventriculo-peritoneal shunt, ventriculo-pleural shunt, limbo-peritoneal, shunt and other types of extracranial shunts which are rarely used. In current practive, the ventriculo-peritonial shunt is the type most commonly used for the treatment of various kinds of hydrocephalus. However clinical experience has proven that it is still not an ideal procedure. The major shortcoming lies in the fact that the extracranial tube consists of a ventricular tube, a reservoir and a distal tube. The valve in the reservoir or in the distal tube and the anti-siphon device, is often found unable to regulate and draw an appropriate quantity of CSF for proper circulation. Various complications relating to over drainage of CSF in the ventricies may result, such as chronic subdural hemorrhage, slit ventricle syndrome, isolated enlargement of the fourth ventricle, etc. In addition, defects may also be caused by a defective shunting tube. Such defects may include both obstruction at the end of the ventricular catheter, and breaking and/or falling off of the joining parts which link the vertricular tube, the reservoir, and the distal tube. In the ventriculo-peritoneal shunt which is most commonly used, there are also possibilities of various peritoneal complications, such as inguinal hernial, hydrocele, false pocket inside the peritoneum (pseudocyst) and peritonitis caused by shunt infection, perforation of the intestine or perforation of the peritoneal wall by a shunting tube, twisting of intestine (volvulus), etc. Infection after a shunting procedure (shunt infection) is a serious complication. The infection after ventriculo-peritoneal shunt operation usuallu causes venticulistis and peritonitis (inflammation of the ventricular system of the brain and the peritoneal cavity). In view of these defects, it is apparent that the ventriculo-peritoneal shunting procedures which are commonly used at the present time are still not adequate.

In addition to the aforementioned extracranial shunting procedures, intracranial shunting procedures are also available. The basic theory of these intracranial shunting procedures is the use of a surgical operation or a shunting tube to enable the CUS to bypass the obstruction and circulate to the subarachnoid space, so as to be absorbed by the arachnoid villi. This is consistent with the physiology of normal circulation of the CSF.

Intracranial shunting procedures include (1) ventriculo-sagittal sinus shunt, (2) ventriculo subarachnoid space shunt, (3) ventriculo-cisternal shunt, (4) the third ventriculostomy, and (5) the third-fourth ventricular shunt. Senn in 1908 and Forrest in 1957 both reported the results of treating hydrocephalus by using a perforated rubber tube in their ventriculo-subdural shunting procedures. The theory of these shunting procedures is to circulate the CSF through the shunting tube to the subarachnoid space on the surface of the cerebrum to be further absorbed by the arachnoid villi for blood circulation. However, no further report has been made since 1957. Presently, the above mentioned shunting procedures numbers (3), (4) and (5) are still occasionally used by some neurosurgeons, but they are not always applicable for the treatment of all forms of hydrocephalus.

In view of the defects described in the preceding sections prior art and techniques concerning the treatment of hydrocephalus by the application of extracranial shunts and the intracranial shunts, the inventors have devoted themselves, with their years of accumulated experimental and clinical experience, to the development of the present invention which will provide better treatment of hydrocephalus and ultimately be of great benefit to patients.

The main novelty of the present invention is that it provides certain features which should be found in an ideal shunting tube that will shunt only the excessive CSF an then still maintain a normal intracranial pressure, and cause fewer consequent complications by avoiding those problems associated with the reservoir, connector, and distal end.

Such a feature of the present invention is its adoption of an intracranial ventriculo-subdural shunt which is compatible with the physiology of the circulation of CSF.

Still another feature of the present invention is found in its shunting tube which is composed of a thin film and a ventricular tube, made of hydrogel such as hydrophilic polymer material which has proved to be of obvious benefit in medical treatment of this condition.

BRIEF DESCRIPTION OF THE DRAWINGS

FIG. 1: View of a longitudinal section of the structure of the present invention.

FIG. 2: Perspective view of the present invention.

FIGS. 4A-E: A lost-wax casting process to form ventricular tube of the present invention.

DETAILED DESCRIPTION OF THE INVENTION

Please refer to FIG. 1. and FIG. 2. The present invention is composed entirely of poly-2-hydroxyethyl methacrylate (hereinafter, PHEMA). Its structure is comprised of a thin film 10 and a ventricular tube 12. The thin film 10 is set at the top end of the ventricular tube 12, with the top hole 11 of the ventricular tube 12 formed at the center of the thin film 10. The other end of the ventricular tube 12 is sealed off, and a number of side holes 13 are set around the sealed end. The actual specifications of the present invention are for a thin film 10, 50 mm in width and 0.5 mm in thickness, and a ventricular tube 50-90 mm in length (varying in dimension according to size of the brain and age of the patient), with an internal diameter of 1.2 mm and an external diameter of 2.5 mm. The side holes, which are placed in the 10 mm closest to the sealed end, are approximately 0.8 mm in diameter, and they are known as "fluid connection inlet holes".

Figure 3:
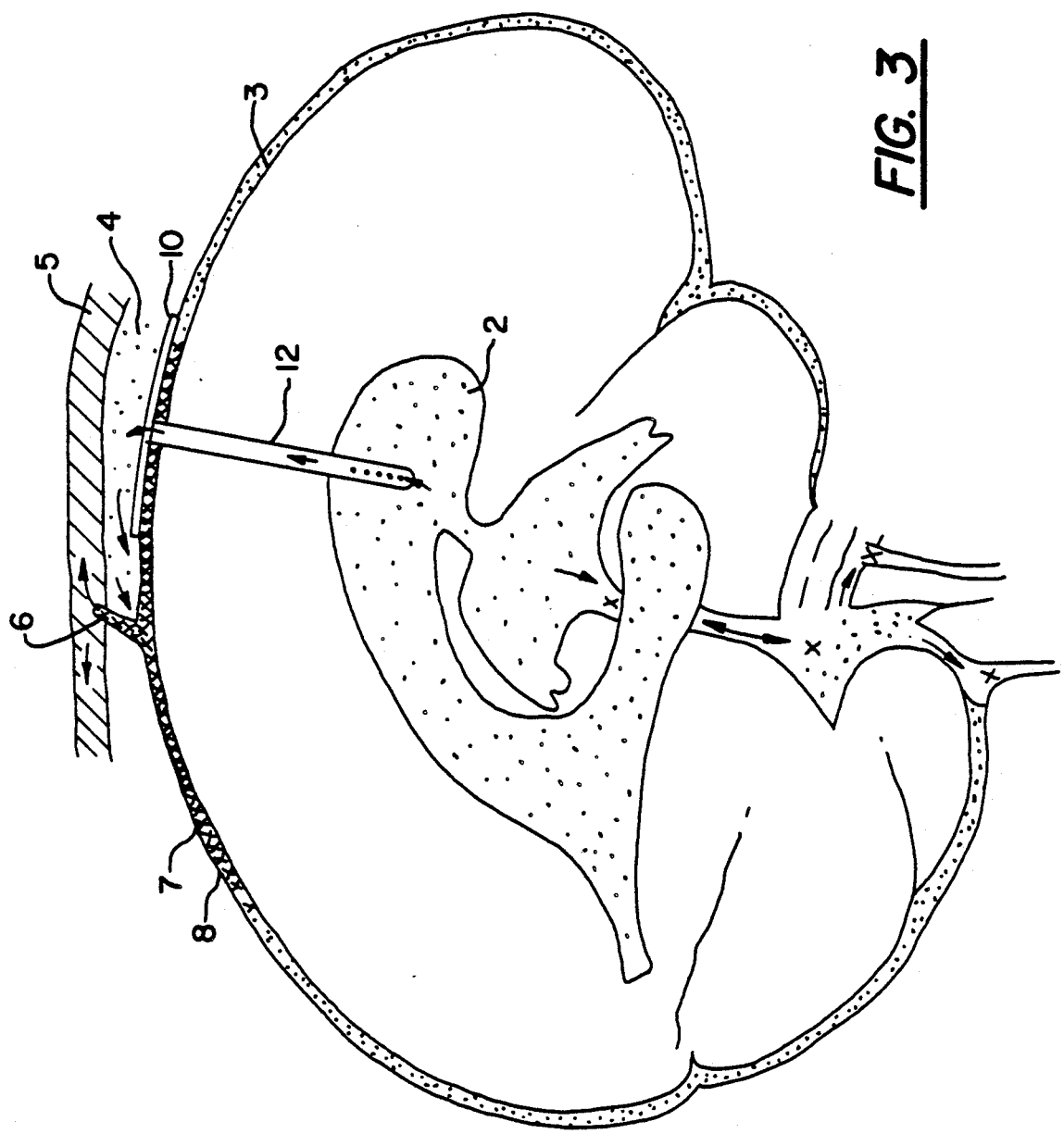
FIG. 3: Drawing of the present invention.

The present invention is a shunting tube which is used for a ventriculo-subdural space shunt in intracranial shunting procedures. (Please refer to FIG. 3.) It can be seen that No.2 refers to the ventricular system, No.3 refers to the surface of the convexity of the brain, No.4 refers to the subdural space, No.5 refers to the safittal sinus, No.6 refers to the arachnoid villi, No.7 refers to the arachnoid, No.8 refers to the subarachnoid space, and X denotes the obstruction focus. When the circulation route of the CSF extending from the ventricle 2 through the cisterns and the subarachnoid space at the base of the brain encounters an obstruction focus X, then expansion of the ventricular system results, which may result in an increase in intracranial pressure and cause hydrocephalus. In FIG. 3, the present invention has been implanted in the intracranium of a patient with hydrocephalus, so that the ventricular tube 12 has pierced into the ventricular system 2, while the thin film 10 adheres closely to the arachnoid 7 on the convexity of the brain. At this time, a passage will be formed by the ventricular tube 12 to enable the drainage of CSF in the ventricle through side holes 13, and this CSF will be discharged through top hole 11 to the subdural space at convexity 3 of the brain. Through arachnoid lacerations or openings during the shunting procedure, the CSF in the subdural space will then enter into the subarachnoid space 8 and be further absorbed by the arachnoid villi. Therefore, the accumulated CSF in the ventricle will be shunted away to restore and then maintain normal intracranial pressure.

Figure 4C:
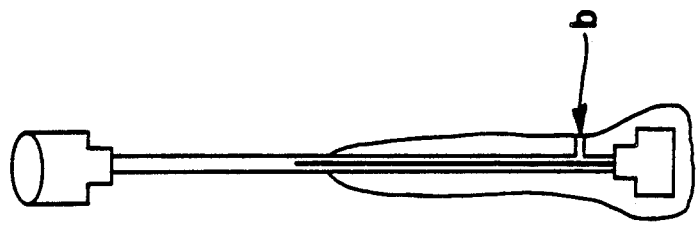
Figure 4B:
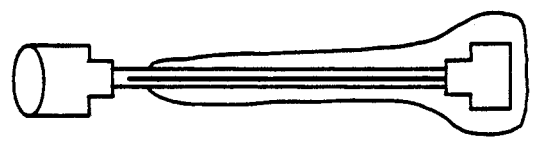
Figure 4A:
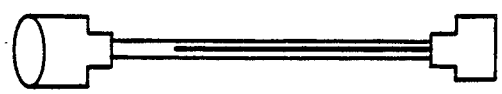

The present invention is fabricated either fully or partially by lost-wax casting process. (Please refer to FIGS. 4A-E). The method consists of the following procedure: A. A thin film is cast by photopolymerization between two glass plates, 50 mm in width and 0.5 mm in thickness. FIG. 4A shows the casting device (hypodermic needle). B. A ventricular tube 12 is made using the lost-wax casting process, 50-90 mm in length, internal diameter 1.0-2.0 mm, enternal diameter 2.5-3.5 mm. FIG. 4B shows the casting device with a wax layer. Fluid collection inlet holes are punctured in the area 10 mm from the lower end of the tube as shown by arrow b. These small holes 13, with diameter about 0.8 mm, are bored through. The other end is sealed off by tape. The lower end of the tube is then sealed with UV radiation under $N_2$ purge, as shown in FIG. 4E the tubes are exposed to UV radiation while being rotated for example by a motor at less than 20 rpms. C. The other (open) end is connected with the hole 11 in the thin film 10. The hydroxyethyl methacrylate mixture is then applied, for example injected slowly, to the connecting surface, and the area is then polymerized under $N_2$ purge to form a firm bond.

The advantages of the present invention lie in the following:

1. The accumulated intraventricular cerebrospinal fluid will bypass the obstruction in the CSF circulation inside the ventricles or at the base of the brian, directly reach the subdural space on the convexity of the brain, go through the subarachnoid space through the arachnoid tearing, and be further absorbed by the arachnoid villi for blood circulation.

2. The absorption of the CSF is mainly regulated by the arachnoid villi in a similar manner to when it is regulated under a normal condition. No valve will be required and no overdrainage will occur.

3. No fluid storage ball and distal tube will be required. Therefore, various complications which relate to storage ball and distal tube will not occur.

4. The shunting tube is made of principally poly-2-hydroxyethyl methacrylate material, and has excellent tissue compatibilty devoid of any side effects. This has been found to be better than the conventional extracranial shunting tubes made of organo - silicon rubber. A further advantage is that the use of the lost wax process to fabricate the device in various specifications reduces or eliminates inter connectors that may come loose or break during service in the human body.

Although it is possible that the shunting tube and the shunting procedures presented by this invention may lead to complications such as obstruction at the ventricular end of the tube, obstruction at the exit of the subdural space, and infection after the shunting procedure, such complications are unfortunately unavoidable in any shunting procedures for hydrocephalus.

Summarising the above description, it can be seen that the present invention aims at providing an improved shunt tube which is simple in its structure and intrinsic natune, and which will provide obvious benefits for the treatment of hydrocephalus. Its effectiveness has been demonstrated in extensive clinical results of its practical effects.

We claim:

1. An intracranial shunting tube consisting essentially of a thin film and a ventricular tube, said ventricular tube having an open top end, a closed bottom end, a central axis, and a plurality of side holes defined therethrough adjacent said closed end, said thin film being provided at said open end of said ventricular tube so as to extend radially outwardly from said open end, the shunting tube being implantable into the brain of a patient with hydrocephalus so as to bypass ventricular cerebrospinal fluid (CSF) to the subdural space on the surface of the brain of the patient and shunt the CSF fluid from the overdistented ventricle of the patient in order to maintain a normal intracranial pressure.

2. An intracranial shunting tube as in claim 1, wherein said ventricular tube is formed principally from cross-linked poly-2-hydroxyethyl methracylates hydrogel material.

* * * * *